(12) United States Patent
Wang et al.

(10) Patent No.: US 11,026,694 B2
(45) Date of Patent: Jun. 8, 2021

(54) LEFT ATRIAL APPENDAGE OCCLUDER

(71) Applicant: HANGZHOU NUOMAO MEDTECH CO., LTD., Zhejiang (CN)

(72) Inventors: Yongsheng Wang, Zhejiang (CN); Tingchao Zhang, Zhejiang (CN); Zhenjun Zi, Zhejiang (CN)

(73) Assignee: HANGZHOU NUOMAO MEDTECH CO., LTD., Hangzhou (CN)

( * ) Notice: Subject to any disclaimer, the term of this patent is extended or adjusted under 35 U.S.C. 154(b) by 340 days.

(21) Appl. No.: 15/746,132

(22) PCT Filed: Jul. 19, 2016

(86) PCT No.: PCT/CN2016/090413
§ 371 (c)(1),
(2) Date: Jan. 19, 2018

(87) PCT Pub. No.: WO2017/016411
PCT Pub. Date: Feb. 2, 2017

(65) Prior Publication Data
US 2018/0206850 A1 Jul. 26, 2018

(30) Foreign Application Priority Data
Jul. 28, 2015 (CN) .......................... 201510450430.8

(51) Int. Cl.
*A61B 17/12* (2006.01)
(52) U.S. Cl.
CPC ........ *A61B 17/12122* (2013.01); *A61B 17/12* (2013.01); *A61B 17/12031* (2013.01); *A61B 17/12145* (2013.01)
(58) Field of Classification Search
CPC ........ A61B 17/12031; A61B 17/12122; A61B 17/12168; A61B 17/12172;
(Continued)

(56) References Cited

U.S. PATENT DOCUMENTS

2007/0066993 A1 3/2007 Kreidler
2013/0131717 A1* 5/2013 Glimsdale ........ A61B 17/12122
606/213
(Continued)

FOREIGN PATENT DOCUMENTS

CN 101449986 A 6/2009
CN 103598902 2/2014
(Continued)

OTHER PUBLICATIONS

English Machine Translation of CN-104398284-A (Year: 2015).*
(Continued)

*Primary Examiner* — Diane D Yabut
*Assistant Examiner* — Christian D Knauss
(74) *Attorney, Agent, or Firm* — Hauptman Ham, LLP

(57) ABSTRACT

A left atrial appendage (LAA) occluder is provided. The LAA occluder includes a sealing disc and an anchoring device, both of which are mutually connected; a part where an LAA cooperates with the anchoring device is an anchoring net, and the anchoring net is of a backboneless structure. The whole anchoring device is of the backboneless structure. The anchoring device is formed by weaving super elastic metal wires or shape memory alloy wires, a distal end of the anchoring device is opened, and a proximal end of the anchoring device is constricted and is connected with the sealing disc to form a conical net. The distal end of the anchoring device is opened and is rolled towards the proximal end to form the anchoring net, and the anchoring net surrounds the conical net. The anchoring net is connected with the conical net through an arc transition area.

19 Claims, 15 Drawing Sheets

(58) Field of Classification Search
CPC ...... A61B 17/0057; A61B 2017/00575; A61B 2017/00588; A61B 2017/00592; A61B 2017/00597; A61B 2017/00606; A61B 2017/00601; A61B 2017/0061; A61B 2017/00615; A61B 2017/00625; A61B 2017/00632; A61B 2017/00867; A61B 17/12022; A61B 17/12027; A61B 17/12109; A61B 17/12133
See application file for complete search history.

(56) References Cited

U.S. PATENT DOCUMENTS

| | | | | |
|---|---|---|---|---|
| 2013/0218193 | A1* | 8/2013 | Erzberger | A61B 17/12172 606/200 |
| 2013/0296912 | A1* | 11/2013 | Ottma | A61B 17/0057 606/191 |
| 2014/0257361 | A1* | 9/2014 | Prom | A61B 17/12022 606/198 |
| 2015/0366649 | A1* | 12/2015 | Tafti | A61F 2/01 606/200 |
| 2017/0325824 | A1* | 11/2017 | Li | A61B 17/12168 |

FOREIGN PATENT DOCUMENTS

| | | | |
|---|---|---|---|
| CN | 203634235 | | 6/2014 |
| CN | 104274224 | | 1/2015 |
| CN | 104352260 | | 2/2015 |
| CN | 104352261 | | 2/2015 |
| CN | 104398284 | | 3/2015 |
| CN | 104398284 A | * | 3/2015 |
| CN | 204246182 | | 4/2015 |
| CN | 104958087 | | 10/2015 |
| CN | 105054985 | | 11/2015 |
| CN | 204814031 | | 12/2015 |
| CN | 204971418 | | 1/2016 |
| DE | 102012003021 A1 | | 10/2012 |
| EP | 1982655 A1 | | 10/2008 |
| WO | 2013040431 A1 | | 3/2013 |

OTHER PUBLICATIONS

International search report dated Oct. 31, 2016 from corresponding application No. PCT/CN2016/090413.

Office Action dated Nov. 4, 2016 from corresponding application No. CN 201510450430.8.

Extended European search report issued in corresponding European application No. 16829777.8 dated Mar. 19, 2019.

* cited by examiner

LEFT ATRIAL APPENDAGE OCCLUDER

RELATED APPLICATIONS

The present application is a National Phase of International Application Number PCT/CN2016/090413, filed Jul. 19, 2016, and claims the priority of China Application No. 201510450430.8, filed Jul. 28, 2015.

TECHNICAL FIELD

The present disclosure relates to the technical field of medical apparatuses, and in particular to a left atrial appendage (LAA) occluder.

BACKGROUND

Atrial fibrillation (AF) is the most common sustained arrhythmia. The number of people with AF increases with the growth of age, and the incidence of AF in people over 75 years old is up to 10%.

When AF occurs, the atrial pulsation rate is up to 300-600 beats per minute. The heart rate is often fast and irregular, and an effective atrial systolic function is lost. In case of AF, the contractility of the LAA is decreased; in addition morphological characteristics of the LAA, and the uneven trabecula in the LAA which make the blood flow generate an eddy in the LAA and the blood flow rate slow down, thus resulting in the formation of thrombus. For patients with nonvalvular AF, more than 90% of left atrium thrombi occur in the LAA, and after the thrombus falls off, the thrombi will enter the cerebral arterial blood vessels through the aorta, thereby causing cerebral embolism, namely stroke.

Currently, to prevent AF patients from the risk of stroke, preventive treatments are clinically performed by mainly utilizing the following three methods: anticoagulant treatment, surgical treatment and percutaneous left atrial appendage occlusion (LAAO) treatment.

The anticoagulant treatment is to restrain blood coagulation by oral anticoagulants (such as warfarin and aspirin), so as to reduce the risk of thrombus formation in the LAA, and then reduce the occurrence probability of stoke. Clinic trials show that the anticoagulant treatment can remarkably reduce the occurrence probability of stroke, but the anticoagulant treatment is a long-term process and also has remarkable complications, mainly including bleeding complications, and even may lead to severe cases.

The surgical treatment includes surgical ablation or suture of LAA. However, surgical trauma is large, and such surgery is generally performed during the valve replacement surgery or the coronary artery bypass graft surgery. Patients, especially elderly patients, generally are hard to accept a simple LAA surgery.

The percutaneous LAAO treatment is to transport and then release a LAA occluder to the LAA located in the left atrium of the heart by utilizing a delivery sheath with a smaller diameter in a percutaneous puncture mode. The LAA occluder can occlude the opening of the LAA to prevent blood flow in the atrium from entering the LAA, thereby preventing thrombus formation and achieving a purpose of preventing AF-induced thromboembolism. Since 2001, the percutaneous LAAO treatment has been in use, and has successively subject to animal experiments and clinical trials. Based on the clinical trails, the LAAO treatment can effectively reduce the occurrence probability of stroke of the AF patients.

In recent years, the percutaneous LAAO treatment has been greatly popularized and applied, and different global manufacturers have also successively launched new products. Currently, an LAA occluder is basically prepared from nickel-titanium alloy and a polymer material tectorial membrane, the nickel-titanium alloy mainly achieves a fixation function, and the polymer material tectorial membrane mainly achieves a blood flow occlusion function.

Based on the design structure, the LAA occluder is mainly classified into two types: the first type is a plug structure, which is directly implanted into the LAA and is provided with barbs for fixing the LAA occluder. The LAA occluder with such structure generally needs to be implanted into a deeper position in the LAA through the delivery sheath, and at this point, the LAA occluder with such structure is easy to pierce the LAA and cannot be repeatedly released.

The second type is a structure including an occluding disc and an anchoring disc, the occluding disc occludes the opening of the LAA in the left atrium, and the anchoring disc is disposed in the LAA and is provided with barbs to fix the occluding disc. The LAA occluder with the second structure mainly utilizes the occluding disc to occlude the LAA; when the occluder needs to be released, it must be ensured that the anchoring disc is reliably fitted and sealed in the opening of the LAA. After released, if the occluding disc cannot be fitted in the opening of the LAA and the anchoring disc cannot be re-withdrawn in the delivery sheath, the surgery may fail, and furthermore, the risk of thrombus formation may be increased. Therefore, it is very important that the anchoring disc can be repeatedly released.

In the related art, there is an anchoring disc that can be repeatedly released. However, the whole anchoring disc is not fixed in the LAA in a force uniform distribution mode, instead of being fixed through several local regions, thereby causing stress concentration in these local regions. Furthermore, the barbs in these local regions may also pierce the wall of the LAA, thereby causing the risk of complications, such as pericardial effusion and the like.

SUMMARY

The present disclosure provides a left atrial appendage (LAA) occluder, which can be uniformly attached to the inner wall of the LAA and can be repeatedly released.

A LAA occluder includes mutually connected sealing disc and anchoring device; a part, cooperating with the LAA, of the anchoring device is an anchoring net, and the anchoring net is of a backboneless structure.

The LAA occluder provided by the present disclosure is transported to the LAA of the heart through a transport catheter in a percutaneous puncture mode, the anchoring device is used for anchoring the whole LAA occluder, and the sealing disc occludes the opening of the LAA to prevent blood flow in the left atrium from entering the LAA, thereby preventing stroke caused by thrombus formation in the LAA of an AF patient.

The anchoring net is net-shaped, and utilizes a backboneless structure, which can be uniformly attached to the inner wall of the LAA so as to achieve the fixation of the occluder at the opening of the LAA; meanwhile, if the position of the sealing disc is improper and the sealing disc cannot completely fit the opening of the LAA to achieve occlusion, the anchoring net can be re-withdrawn and accommodated into the transport device, thereby achieving repeated releasing, and remarkably improving the success rate of the surgery.

Compared with the structure of the anchoring device in the related art, the structure of the anchoring net provided by the present disclosure has the following advantages. The anchoring net and the LAA are in surface contact, so that an anchoring force is uniformly distributed on the contact surface between the anchoring net and the LAA, thereby eliminating local stress concentration, and reducing the risk of piercing the LAA wall.

As an implementation, the anchoring device has a structure rolled from interior to exterior, an inner edge part of the rolled structure is connected with the sealing disc, and a periphery part of the rolled structure is the anchoring net that cooperates with the LAA.

That is, the anchoring device has a bi-layer structure with an inner layer and an outer layer, and the anchoring net is located on the periphery of the inner edge part of the rolled structure.

In one implementation, the anchoring net surrounds at least a half of the axial length of the inner edge part.

In one implementation, the anchoring net surrounds to a part, near the proximal end, of the inner edge part in a rolling manner.

During rolling, the anchoring net should have a sufficiently long extension path and a rolling angle. As an example, by taking the axis of the anchoring device as a reference, the rolling angle of the rolled structure can be larger than or equal to 180 degrees, and further, the rolling angle can be larger than or equal to 270 degrees.

As an implementation, the proximal end of the inner edge part is constricted and is connected with the sealing disc.

The fact that the proximal end is constricted means: one side, near the sealing disc, of the inner edge part is gradually constricted, and then is connected with the sealing disc, or, is connected with the radial center area of the sealing disc.

The specific connection manner may be inseparable fixed connection, such as an integral structure, welding, and the like, or also may be detachable connection, such as fastening, threading or transition connection and the like.

As an implementation, the inner edge part is of a compressible hollow structure, and at least is radial compressible in order to facilitate implantation through a blood vessel.

Further, the inner edge part is of a net-shaped structure or a multi-link structure. As an example, the whole anchoring device is of a backboneless structure. In the present disclosure, the anchoring device does not have the backbone structure. When the anchoring device is implanted into the LAA and interacts with the inner wall of the LAA, the anchoring force is uniformly distributed. Especially, because the anchoring net is of the backboneless structure, the anchoring force is uniformly distributed on the contact surface between the anchoring net and the inner wall of the LAA; the backboneless structure also ensures that the anchoring device has excellent compliance and is easy to be suitable for different internal anatomic structures of the LAA.

In the present disclosure, the backboneless structure means that a backbone structure with a supporting function is not arranged in the anchoring device or the anchoring net, so that the mechanical properties of each part of the anchoring device or the anchoring net can keep uniform, and therefore stress concentration on the backbone structure does not occur.

In the related art, a backbone structure is arranged in the anchoring device. When the backbone structure mutually fits with the inner wall of the LAA, the interaction force between the LAA and the anchoring device is concentrated on the backbone structure, which is easy to cause stress concentration due to the fact that local stress on the inner wall of the LAA is overlarge, and then causes the risk of piercing the LAA.

Optionally, the anchoring net is formed by weaving metal wires or cutting off metal tubes.

The anchoring net is a part, contacting and cooperating with the inner chamber of an LAA inner chamber, of the anchoring device. Other parts of the anchoring device, such as the inner edge part of the rolled structure, and the anchoring net may subject to the same or different processing processes. As an example, the anchoring device is formed by weaving the metal wires or cutting off the metal tubes.

For example, the anchoring device is formed by weaving at least one metal wire, and the metal wire is a super elastic metal wire or a shape memory alloy wire. The anchoring net is nest-shaped (namely bowl-shaped). In order to ensure excellent biocompatibility with the human body and meet mechanical property requirements, the super elastic metal wire or the shape memory alloy wire utilizes a nickel-titanium wire.

The anchoring net has a structure of regularly distributed cells. Each cell utilizes a rhombus or an approximate rhombus structure, the anchoring net is a revolution surface, and intersection points of any latitude circles on the revolution surface and the cells of the anchoring net are uniformly distributed along a rotation axis.

In one implementation, the distal end of the inner edge part is opened and is rolled outwardly towards the proximal end to form the anchoring net, and the anchoring net surrounds the inner edge part. In the present disclosure, the distal end and the proximal end are defined relative to an operator, and in the occluder, the end near the operator is the proximal end and the other end away from the operator is the distal end.

As an example, the anchoring net is connected with the distal end of the inner edge part through the arc transition area.

The anchoring net and the inner edge part smoothly transits through the arc transition area without any sharp parts.

As an example, the inner edge part is in the shape of a cone, a pyramid, a truncated cone, a frustum, a cylinder, a drum or a corrugated pipe.

Constricting trend of one side, near the sealing disc, of the inner edge part may be various, and when the integral constricting trend of the inner edge part is uniformly changing, the inner edge part is integrally cone-shaped.

If the inner edge part is in the shape of a truncated cone, a frustum, a cylinder, a drum or a corrugated pipe, it can be understood that only a tiny area, near the sealing disc, of the inner edge part is constricted, and an area away from the sealing disc takes up most of the inner edge part, which decides the integral shape of the inner edge part.

When the inner edge part is of the net-shaped structure, the inner edge part is the conical net, and the anchoring net and the conical net form the bi-layer structure with an inner layer and an outer layer. The anchoring net is located at the periphery of the conical net, one end of the conical net is a center end connected with the sealing disc, and the anchoring net is connected with the bottom edge (the distal end of the inner edge part) of the conical net through the arc transition area.

The anchoring net is a revolution surface, and generatrix of the revolution surface is a straight line or an arc line.

When the generatrix is the arc line, an opening of the arc line faces the interior of the anchoring net, the anchoring net is in the shape of a curved ring, and the curved ring is smoothly connected with the arc transition area.

When the generatrix is a straight line and is in parallel with the axis, the anchoring net is nest-shaped, and it is smoothly connected with the arc transition area.

When the generatrix is the straight line and is inclined to the axis, the anchoring net is in the shape of the truncated cone, the lower bottom (that is, a bottom with the relatively larger area) of the truncated cone is arranged near the sealing disc, and the upper bottom of the truncated cone is smoothly connected with the arc transition area.

The anchoring device is formed by weaving super elastic metal wires or the shape memory alloy wires, and in one implementation, the opening of the nest-shaped anchoring net is bent inwards to form a constricted area.

The constricted area is radially bent toward the center end, and by virtue of the constricted area, end points of the super elastic metal wires or the shape memory alloy wires are hidden in the anchoring net, so that the probability of direct contact with the inner wall of the LAA is reduced, and damage to the LAA is reduced. Each part of the anchoring net smoothly transits with each other without any sharp parts.

When the occluder provided by the present disclosure is released, the constricted area is firstly released from the transport device. Because the anchoring device is formed by weaving the super elastic metal wires or the shape memory alloy wires, so that the constricted area automatically turns over and curls itself after separated from the transport device. Therefore, the part, in contact with the LAA, of the anchoring device is always an arc transition part, so as to prevent the LAA from being damaged.

In order to ensure that the anchoring net can be reliably fixed in the LAA, the anchoring net is provided with multiple barbs. When the anchoring net is in an axial tension compression state, the barbs are arranged on an inner side surface of the anchoring net. The barbs are inclined along the circumferences of the super elastic metal wires or the shape memory alloy wires; that is, the barbs are everted outwardly in a radial direction of the anchoring net, and the barbs are inclined in an axial direction of the anchoring net.

The barbs provided by the present disclosure can ensure the repeated releasing of the occluder. When the occluder is released in the human body, the barbs can effectively pierce the inner wall of the LAA to anchor the position of the occluder. If the position of the sealing disc is improper and the opening of the LAA cannot be greatly occluded, the occluder needs to be withdrawn and released again. In the occluder withdrawing process, the barbs are located on the anchoring net, namely at the outer layer, when the center end is pulled to withdrawn, the inner layer enters the transport device. The movement direction of the outer layer is opposite to that of the inner layer, when the bi-layer structure is disappeared, the outer layer is also accommodated in the transport device. The barbs are located on the outer layer, and the movement directions of the barbs are opposite to their penetration directions, so the barbs can be smoothly withdrawn from the inner wall of the LAA, and then are accommodated in the transport device in a traction direction.

The barbs are arranged on at least one of the arc transition area, the anchoring net or the constricted area. The barbs are fixed with the metal wires of the anchoring net through a ferrule or in a welding manner.

Each barb is made from one super elastic metal wire or shape memory alloy wire, which is called as a barbed metal wire to distinguish the super elastic metal wires or the shape memory alloy wires of the anchoring net, and the barb metal wire can utilize a nickel-titanium wire. The ferrule can utilize metal materials.

As a first embodiment of the barb, the root of the barb extends to the proximal end (such as the center end of the conical net of the inner layer) of the anchoring device along the attached metal wire, that is, one end of the barb metal wire is fixed with the center end of the anchoring net and is mutually clung to one super elastic metal wire or one shape memory alloy wire of the anchoring net in parallel. On the other end near the barb metal wire. The barb metal wire and the parallel super elastic metal wire or shape memory alloy wire are fixed by utilizing a ferrule (such as a steel bushing) or by welding, and the tail end of the barb metal wire extends beyond the fixed point by 1-5 mm and opens to the exterior of the anchoring net at a certain angle to form the barb.

As a second embodiment of the barb, one end of the barb metal wire is located in the ferrule, and the other end of the barb metal wire extends 1-5 mm from the ferrule, thereby forming the barb.

As a third embodiment of the barb, one end of the barb metal wire is fixedly welded with at least one super elastic metal wire or shape memory alloy wire for weaving the anchoring net, and the other end of the barb metal wire extends 1-5 mm from the ferrule, thereby forming the barb.

In the second embodiment and the third embodiment of the barb, the length of the barb metal wire is relatively shorter, and generally is not more than 10 mm.

In the related art, a flow blocking membrane is merely arranged in the sealing disc, therefore the occlusion effect is limited. In order to ensure that the sealing disc has an excellent occlusion effect, preferably, at least two flow blocking membranes are arranged in the sealing disc. The flow blocking membranes are made from medical polymer materials with excellent flexibility, such as PET, PTFE and the like.

The sealing disc is formed by weaving at least one super elastic metal wire or shape memory alloy wire. The super elastic metal wire or shape memory alloy wire can utilize the nickel-titanium wire.

The sealing disc is of a net-shaped structure. The sealing disc includes a disc surface and a waist part, both of which are mutually connected.

The disc surface is located on one side away from the anchoring net, and the center of the disc surface is provided with a first fixed end for connecting a transport device.

The waist part is located on one side near the anchoring net, and the center of the waist part is provided with a second fixed end for connecting the anchoring net.

In the related art, only one flow blocking membrane is arranged, and there is only disc surface arranged, and therefore the flow blocking membrane is disposed in the disc surface. In the present disclosure, the sealing disc is subject to structure improvement and a waist part capable of accommodating multiple flow blocking membranes is disposed, to order provide multiple flow blocking membranes and ensure that there is no interference among the multiple flow blocking membranes and the multiple flow blocking membranes can cooperate with each other, and remarkably improve the flow blocking effects.

As one implementation, the waist part includes a diffusion section and a body section.

The diffusion section that is radiated outwards from the second fixed end.

The body section that is cylindrical and is located at the periphery of the diffusion section; where a top edge of the body section is connected with the disc surface, and a bottom edge of the body section is connected with an outer edge of the diffusion section.

The diffusion section is radiated and diffused outwardly from the second fixed end so as to form a plane or a conical surface, and the second fixed end can slightly approach the disc surface.

The body section is a revolution surface, and the periphery of the body section is equal to or larger than the periphery of the anchoring net. The top edge of the body section is smoothly connected with the disc surface, and the bottom edge of the body section and the outer edge of the diffusion section are in arc transition.

As an example, two flow blocking membranes are arranged, one flow blocking membrane is arranged on the disc surface, and the other flow blocking membrane is located in the body section or on the diffusion section of the waist part.

The axial length of the disc surface is relatively smaller, so the flow blocking membranes are located in the disc surface; the axial length of the body section of the waist part is relatively larger, so the flow blocking membranes may be arranged in the body section or on the diffusion section of the waist part.

In order to achieve a better flow blocking effect, three flow blocking membranes are arranged; one flow blocking membrane is arranged on the disc surface, one flow blocking membrane is located in the body section of the waist part, and the last one flow blocking membrane is located on the diffusion section.

The LAA occluder provided by the present disclosure can be anchored in the LAA with uniformly distributed force, and can eliminate the local stress concentration; furthermore, the LAA occluder can be repeatedly released and can effectively and reliably occlude the opening of the LAA.

BRIEF DESCRIPTION OF THE DRAWINGS

FIG. 6b is an enlarged diagram of part A in FIG. 6a.

FIG. 7b is an enlarged diagram of part B in FIG. 7a.

FIG. 11b is an enlarged diagram of part C in FIG. 11a.

FIG. 12b is an enlarged diagram of part D in FIG. 12a.

FIG. 13b is an enlarged diagram of part E in FIG. 13a.

FIG. 14b is an enlarged diagram of part F in FIG. 14a.

DESCRIPTION OF THE EMBODIMENTS

The present disclosure is described in detail below in conjunction with accompanying drawings and embodiments.

Embodiment 1

Figure 1:
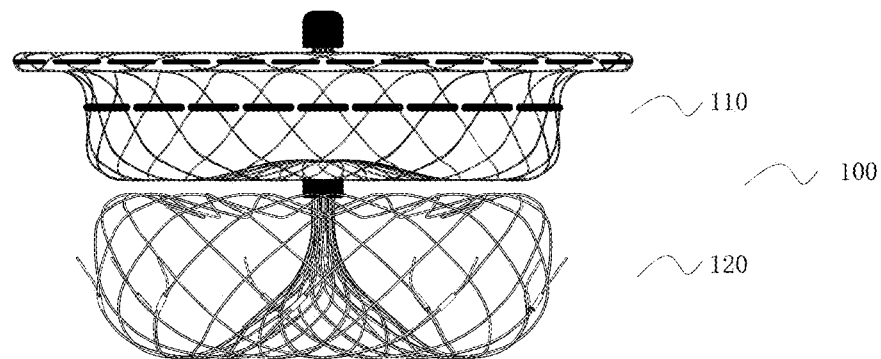
FIG. 1 is an integral schematic diagram of an LAA occluder in embodiment 1.

As illustrated in FIG. 1, a left atrial appendage (LAA) occluder 100 provided by the present disclosure includes a sealing disc 110 and an anchoring device 120.

Figure 2:
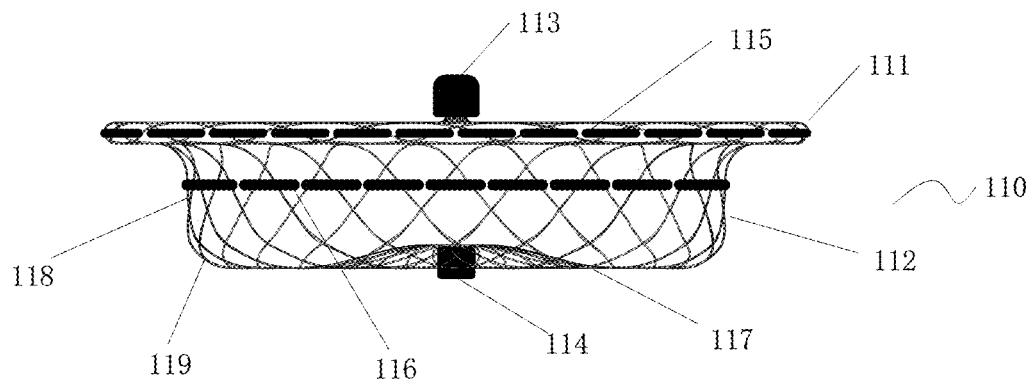
FIG. 2 is a schematic diagram of a sealing disc of the LAA occluder in embodiment 1.

The sealing disc 110 is of a net-shaped structure formed by weaving nickel-titanium wires, as illustrated in FIG. 2, the sealing disc 110 includes a disc surface 111 and a waist part 112. A first fixed end 113 is arranged at the center of the disc surface 111, and a second fixed end 114 is arranged at the center of the waist part 112. One layer of PET flow blocking membrane 115 is sutured in the disc surface 111, and at least one layer of flow blocking membrane 116 is sutured in the waist part 112.

The first fixed end 113 is used for connecting a transport device, and the second fixed end 114 is connected with the anchoring device 120.

As illustrated in FIG. 2, the waist part 112 includes a diffusion section 117 that is radiated outwards from the second fixed end 114, and a body section 118 that is cylindrical and is located on the periphery of the diffusion section 117. The body section 118 has a top edge connected with the disc surface 111, and a bottom edge in transition connection with the outer edge of the diffusion section 117 through a circular arc 119, and the flow blocking membrane 116 in the waist part 112 is located at the axial middle part of the body section 118.

The diffusion section 117 is radiated and diffused outwards from the second fixed end 114 so as to form a plane, and the second fixed end 114 is formed slightly near the disc surface 111 so as to form a sunken area in the plane.

Figure 3A:
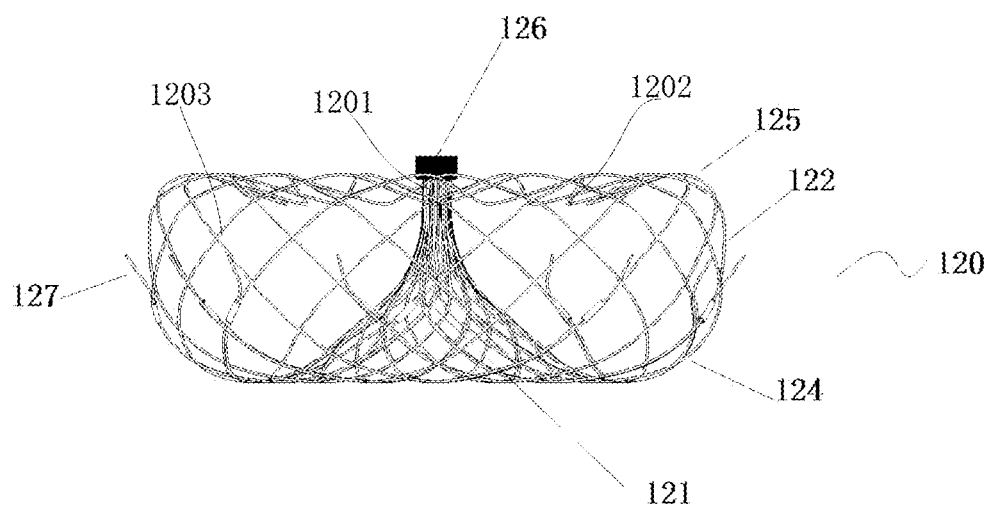
FIG. 3a is a schematic diagram of an anchoring device of the LAA occluder in embodiment 1.
Figure 3B:
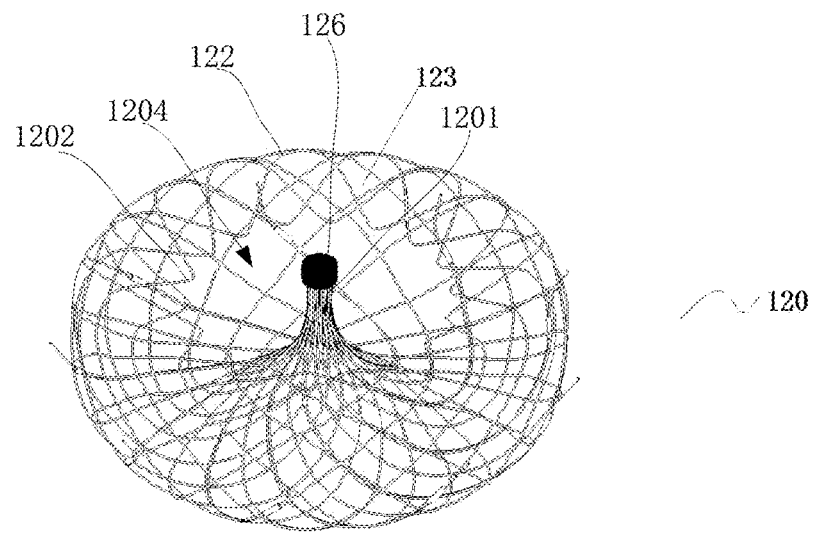
FIG. 3b is a schematic diagram of an anchoring device of the LAA occluder in embodiment 1 (from another perspective).

As illustrated in FIG. 3a and FIG. 3b, the anchoring device 120 is of a net-shaped structure formed by weaving nickel-titanium wires, and the anchoring device 120 is in the shape of a nest 122 (namely bowl-shaped). The anchoring device 120 is of a backboneless structure, that is, no framework is arranged in the anchoring device 120 for supporting.

In the embodiment, the anchoring device 120 is of a bi-layer structure. Specifically, the anchoring device 120 comprises a first end portion 1201, a second end portion 1202 and a body 1203 between the first end portion 1201 and the second end portion 1202. The first end portion 1201 of the anchoring device 120 is constricted (gathered together) and extends towards the sealing disc 110 so as to form an inner edge part, and in the embodiment, the inner edge part is a conical net 121. A proximal end of the conical net 121 is constricted (gathered together) to form a center end 126 connected with the sealing disc 110. A distal end of the conical net 121 is opened, and is rolled outwardly towards the proximal end, so as to form an anchoring net 122; the anchoring net 122 is located on the periphery of the conical net 121. In the embodiment, the anchoring net 122 is connected with the opening of the distal end of the conical net 122 through an arc transition area 124. In other words, as illustrated in FIG. 3a, the first end portion 1201 is gathered together to form the center end 126, the body 1203 extends outwards from the first end portion 1201 to form the conical net 121, and then gradually reverses outwards and extends towards the first end portion 1201 to form the anchoring net 122 surrounding the conical net 121. As illustrated in FIG. 3b, the anchoring net 122 defines an opening 1204 at the second end portion 1202, and the center end 126 extends out of the opening 1204 to connect with the second fixed end 114 of the sealing disc 110. Six barbs 127 are uniformly distributed on the outer surface of the nest-shaped anchoring net 122. The anchoring net 122 surrounds at least a half of the axial length of the inner edge part, and in the embodiment, the anchoring net 122 surrounds to a part, near the proximal end, namely the center end 126, of the inner edge part.

The opening of the nest is bent inwards to form a constricted area 123 (that is, one end, near the sealing disc 110, of the nest 122 radially extends towards the center end 126 so as to form the constricted area 123). The center end 126 is located at an axial end of the conical net 121, and the constricted area 123 and the net 122 are in smooth transition connection through an arc transition area 125.

Figure 4:
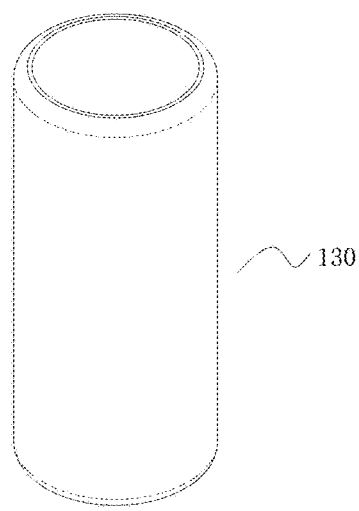
FIG. 4 is a schematic diagram of a steel bushing for connecting the sealing disc with the anchoring device in embodiment 1.

As illustrated in FIG. 4, the second fixed end 114 of the sealing disc 110 and the center end 126 of the anchoring device 120 are welded together with each other through a steel bushing 130 so as to form the LAA occluder 100 illustrated in FIG. 1.

In the embodiment, the anchoring net 120 is formed by weaving 24 nickel-titanium wires, where six nickel-titanium wires are used for forming the barbs, and the residual 18 nickel-titanium wires are used for weaving a frame of the anchoring device, and the diameter of the nickel-titanium wires for forming the barbs and the diameter of the nickel-titanium wires for forming the frame are same.

Figure 5:
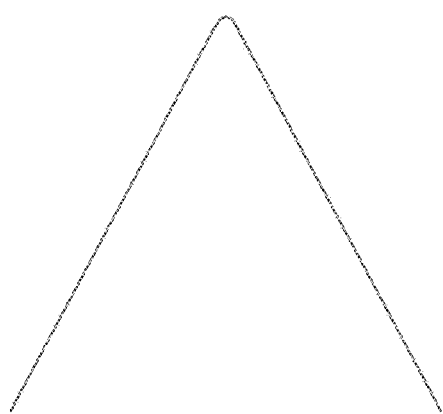
FIG. 5 is a structural schematic diagram of a nickel-titanium wire for weaving a frame of the anchoring device in embodiment 1.
Figure 6A:
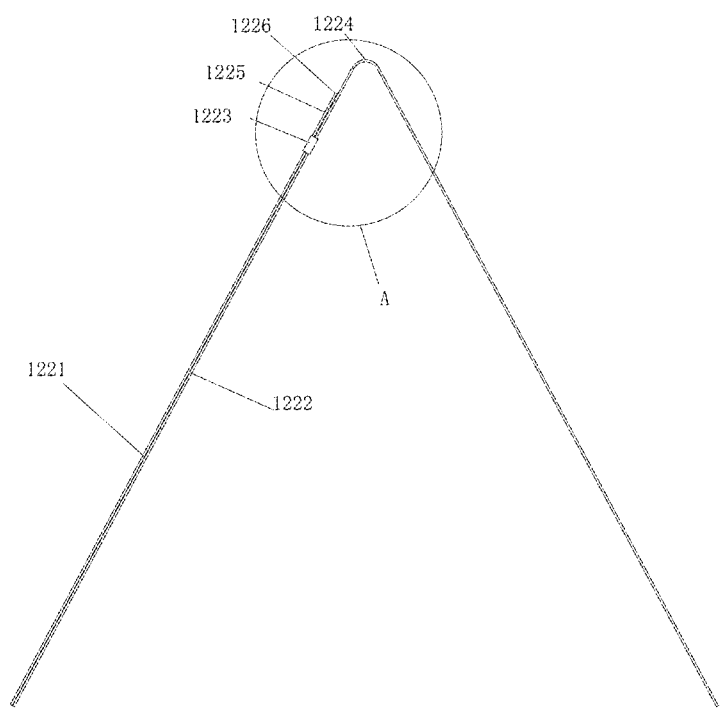
FIG. 6a is a schematic diagram of a connection between a nickel-titanium wire as a barb and the nickel-titanium wire for weaving the frame of the anchoring device in embodiment 1.
Figure 6B:
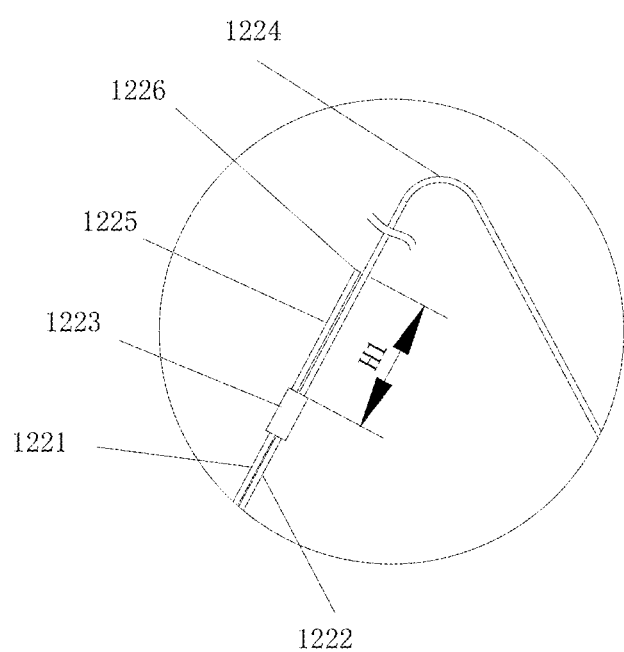

As illustrated in FIG. 5, the nickel-titanium wires for weaving the frame of the anchoring device are pre-molded into a reversed V shape, and there are totally 18 reversed V-shaped nickel-titanium wires. As illustrated in FIG. 6a and FIG. 6b, each nickel-titanium wire 1221 for forming the barb and one side 1222 of one reversed V-shaped nickel-titanium wire for weaving the frame of the anchoring device are in parallel arrangement (both of which can be fixed or not fixed according to requirements during parallel arrangement), and they are pressed and fixed by a steel bushing (made of a stainless steel material) 1223. The steel ferrule 1223 is formed near an apex 1224, at which two sides of the reversed V-shaped nickel-titanium wire are intersected.

As illustrated in FIG. 6b, an end part 1225, extending from the steel bushing 1223, of the nickel-titanium wire 1221 forms a barb 127, the length of the end part 1225 is 2 mm (namely H1=2 mm in FIG. 6b), and a distance between the end point 1226 of the end part 1225 and the apex 1224 of the reversed V-shaped nickel-titanium wire is 8 mm.

Figure 7A:
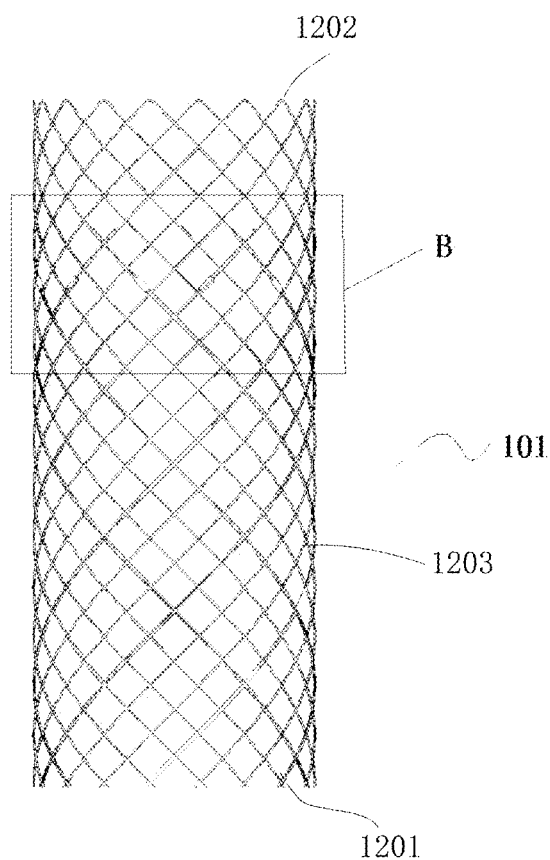
FIG. 7a is a schematic diagram of a net tube that is woven in an anchoring device manufacturing process in embodiment 1.
Figure 7B:
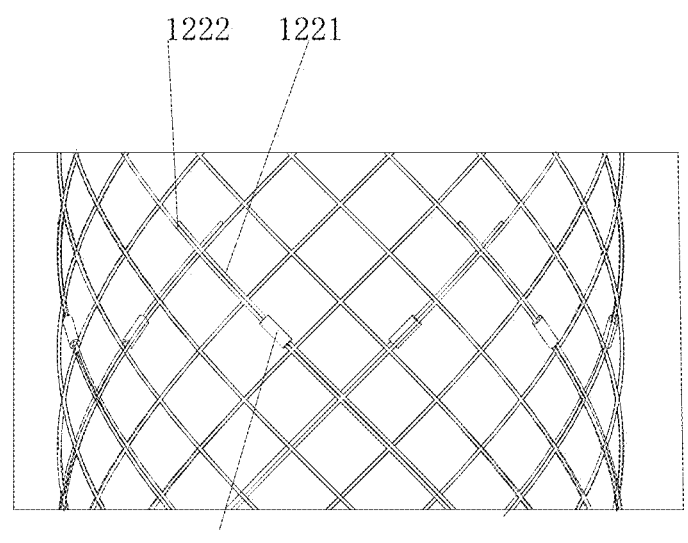
Figure 8:
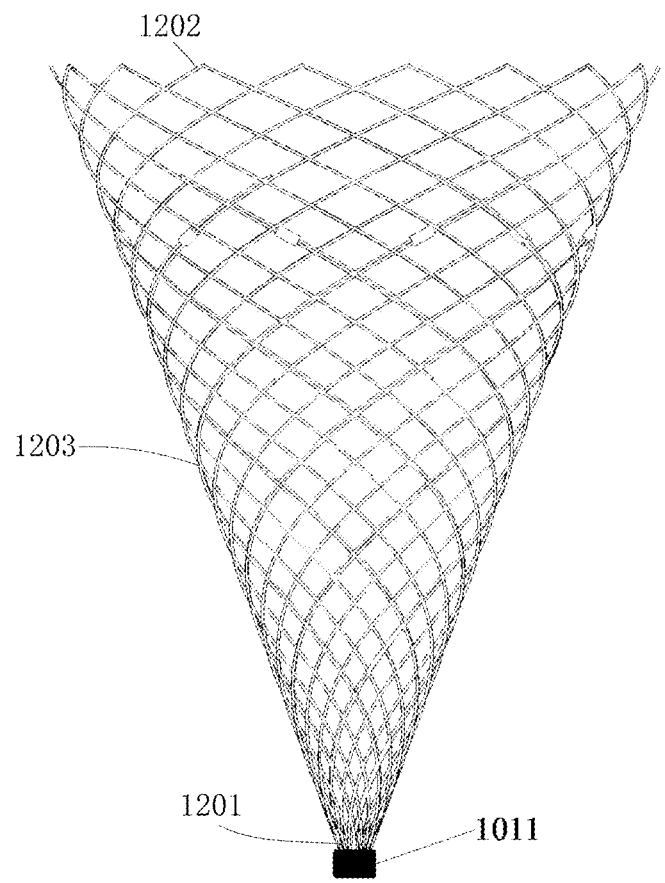
FIG. 8 is a schematic diagram of the woven net tube after its one end is constricted and welded in embodiment 1.

After the nickel-titanium wires are prepared, all nickel-titanium wires are firstly woven and shaped to form a straight cylindrical net tube 101, and as illustrated in FIG. 7a and FIG. 7b, the six nickel-titanium wires for forming the barbs are uniformly distributed along the circumference of the net tube 101. Corresponding to the anchoring net 122 as illustrated in FIGS. 3a and 3b, the net tube 101 the first end portion 1201, the second end portion 1202 and the body 1203 between the first end portion 1201 and the second end portion 1202. After the net tube 101 is manufactured, as illustrated in FIG. 8, first, the tail end 1011 (first end portion 1201) of the net tube 101 can be fixed and welded by utilizing a stainless steel bushing, then the net tube 101 is formed into the shape of an anchoring device illustrated in FIG. 3 through molds and high-temperature heating, and meanwhile, the end part 1225 is partially expanded outward for at a certain angle (such as 30 degrees) to form the barb 127.

As illustrated in FIG. 1, in the embodiment, the barbs 127 are uniformly distributed along the circumference of the anchoring net, radially and externally rolled along the anchoring net 122, and axially inclined along the anchoring net 122. More intuitively, as illustrated in FIG. 7a and FIG. 7b, in an anchoring device 120 manufacturing process, the nickel-titanium wires for forming the barbs 127 and the nickel-titanium wires for forming the frame of the anchoring device are arranged in parallel, and the tail ends of the nickel-titanium wires for forming the barbs 127 are tilted up, so that an angle (which is not zero) is formed between each nickel-titanium wire for forming the barb 127 and each nickel-titanium wire for forming the frame of the anchoring device as illustrated in FIG. 3a.

In the embodiment, the diameter of the nickel-titanium wires for forming the barbs may be larger than that of the nickel-titanium wires for forming the frame of the anchoring device. The number of the barbs on the anchoring net may be 3, 9 or other numbers in a uniform distribution manner, and the frame of the anchoring device may be woven by using 36 or other numbers of the reversed V-shaped nickel-titanium wires.

In the embodiment, the steel bushings 1223 for fixing the barbs 127 and the steel bushing for anchoring the tail end 1011 of the net tube 101 may be made from nickel-titanium or other metals meeting the biocompatibility requirements.

Figure 9:
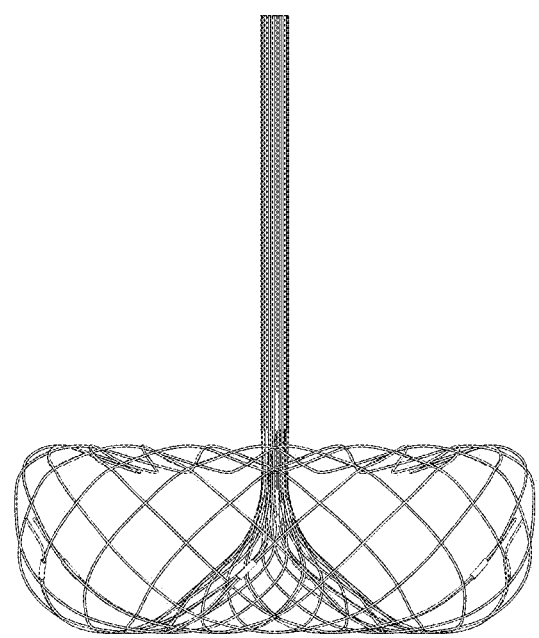
FIG. 9 is a schematic diagram of a center end of the anchoring device without welding the steel bushing in embodiment 1.

In the embodiment, after the manufacturing of the net tube 101 woven by the nickel-titanium wires is completed, the net tube 101 can be first formed into a shape illustrated in FIG. 9, and then the center end is welded and fixed by the metal bushing to form a shape illustrated in FIG. 3. After the manufacturing is completed, the whole anchoring device is of a backboneless structure, so that mechanical properties of each part of the anchoring device are uniform.

Figure 10:
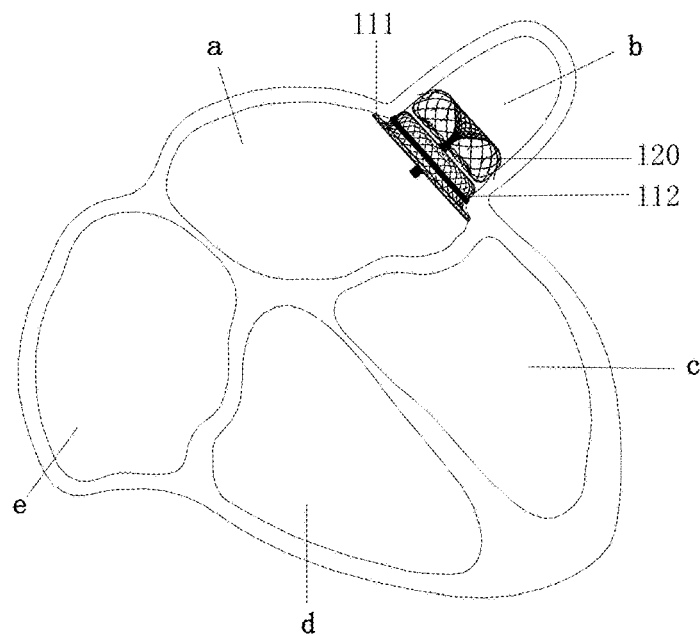
FIG. 10 is a schematic diagram of the LAA occluder released in the LAA in embodiment 1.
Figure 11A:
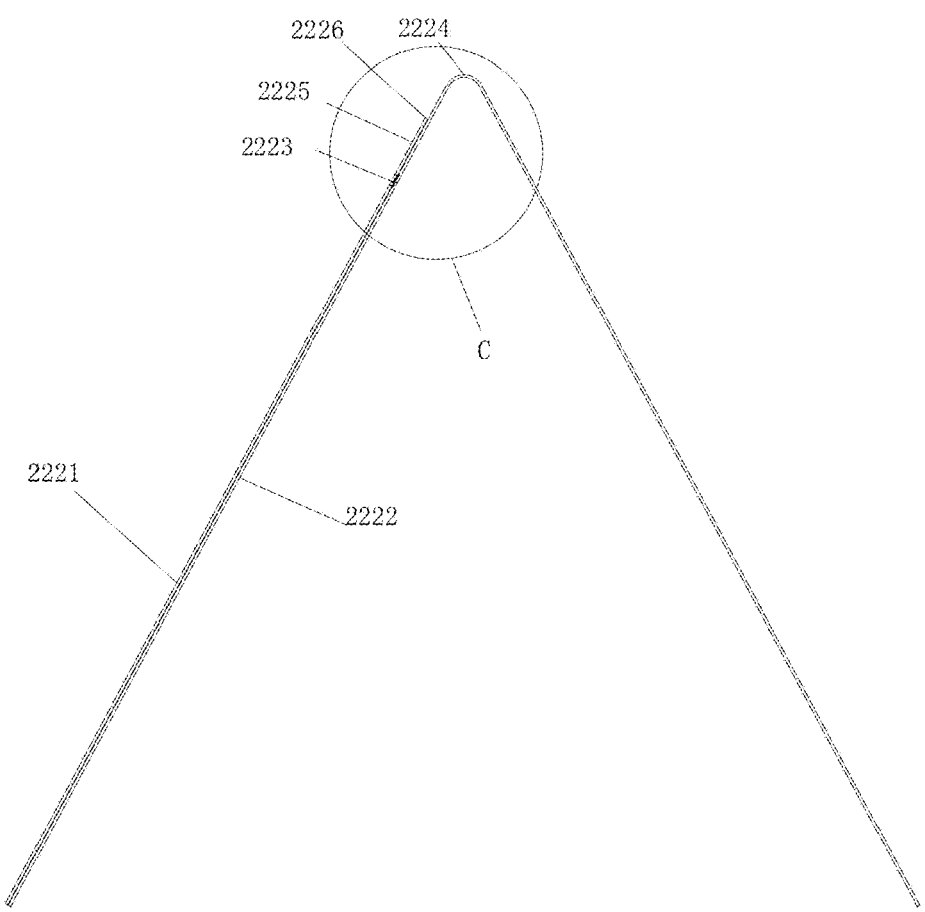
FIG. 11a is a schematic diagram of a connection between a nickel-titanium wire as a barb and a nickel-titanium wire for weaving a frame of an anchoring device in embodiment 2.
Figure 11B:
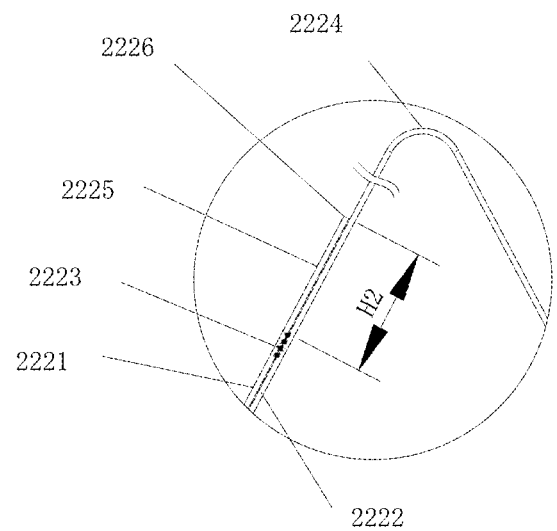
Figure 12A:
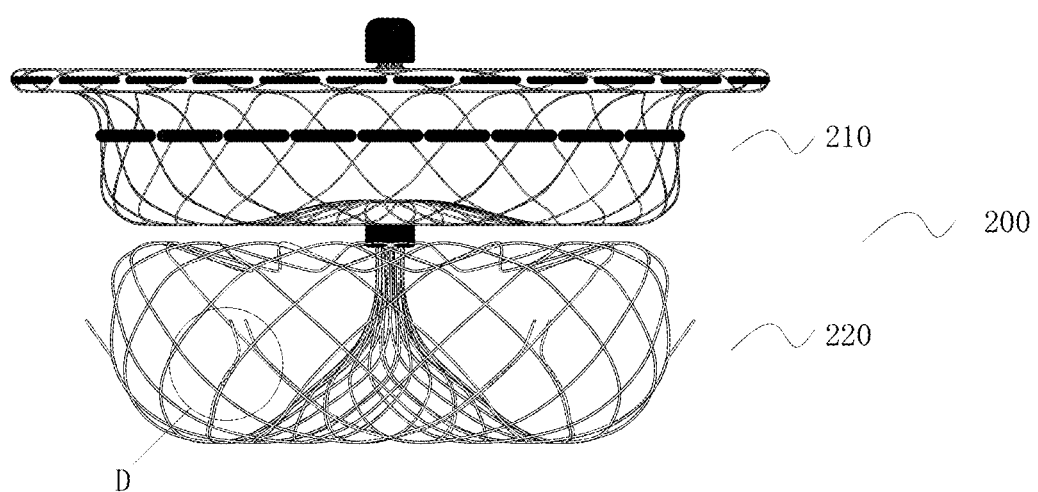
FIG. 12a is a schematic diagram of an LAA occluder in embodiment 2.
Figure 12B:
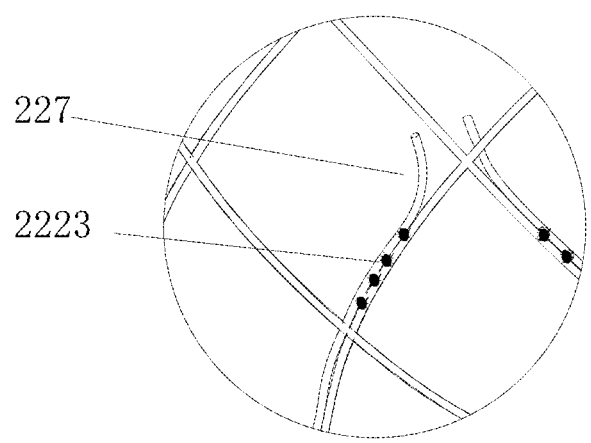
Figure 13A:
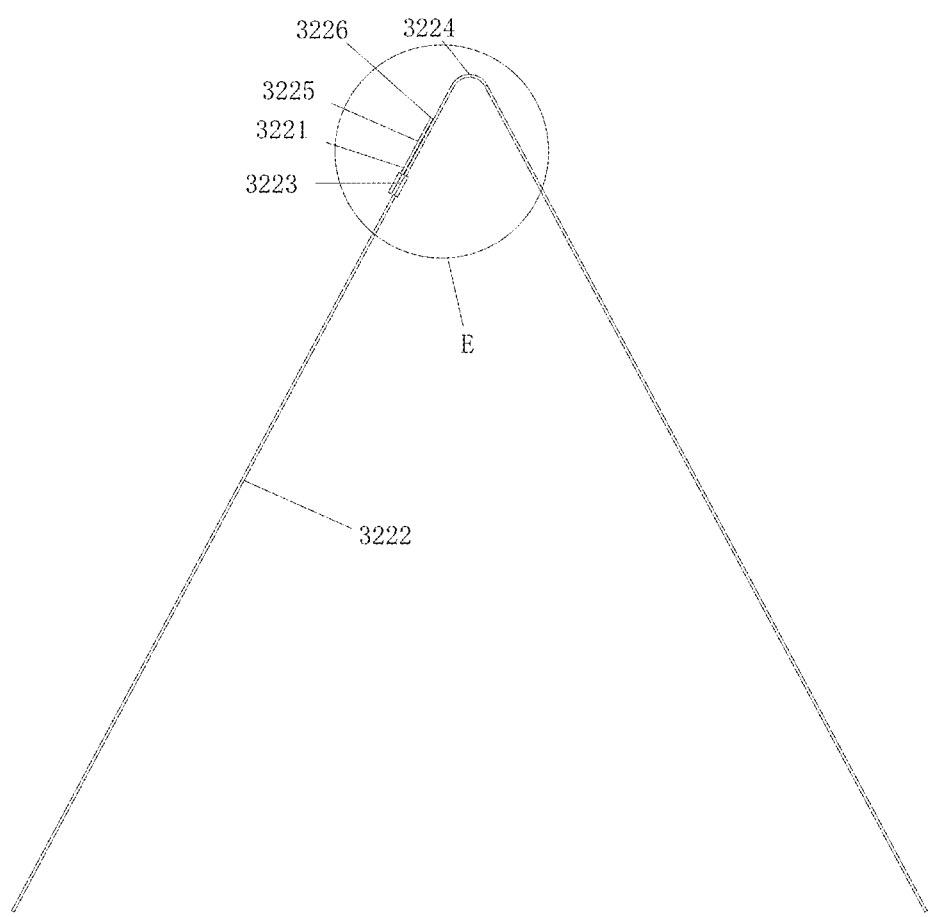
FIG. 13a is a schematic diagram of a connection between a nickel-titanium wire used as a barb and a nickel-titanium wire for weaving a frame of an anchoring device in embodiment 3.
Figure 13B:
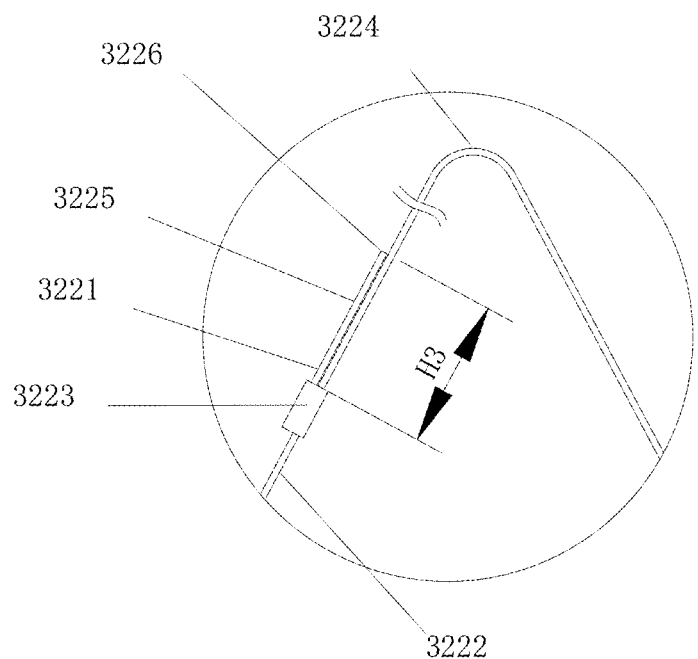
Figure 14A:
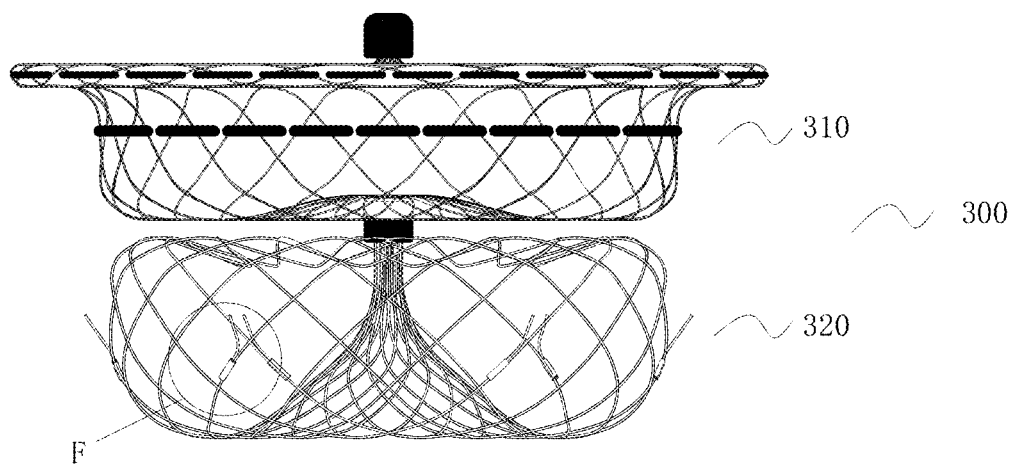
FIG. 14a is a schematic diagram of an LAA occluder in embodiment 3.
Figure 14B:
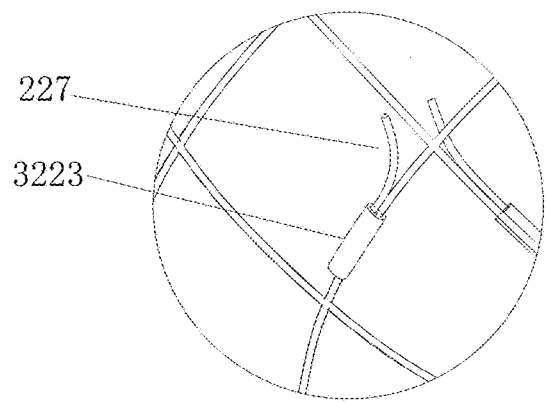

In the embodiment, the LAA occluder 100 can be enclosed in a transport device with a small diameter (such as an inner diameter of 9 F), then sequentially enter superior vena cava by virtue of femoral vein puncture, the right atrium, and the left atrium by virtue of interatrial septal puncture. When the LAA occluder 100 is released, first, the anchoring device 120 is released in the LAA, and the barbs 127 on the anchoring net 122 hook the inner wall of the LAA. Then the waist part 112 of the sealing disc 110 is released at the opening of the LAA, and the disc surface 111 of the sealing disc 110 is released at the opening of the left atrium, thereby sealing the opening of the LAA. After the releasing is completed, the LAA occluder is removed from a connection part with the transport device. FIG. 10 is a schematic diagram of the finally released LAA occluder. In FIG. 10, a represents the left atrium, b represents the LAA, c represents the left ventricle, d represents the right ventricle, and e represents the right atrium.

In the embodiment, the anchoring device 120 of the LAA occluder 100 is in a uniform mesh shape woven by the nickel-titanium wires, and the nest-shaped anchoring net 122 on the outer layer of the anchoring device 120 can uniformly come into contact with the inner wall of the LAA to ensure that the pressure is uniformly applied to the inner wall of the LAA and no local stress concentration occurs.

In the embodiment, the barbs 127 on the anchoring net 122 of the LAA occluder 100 are made from the nickel-titanium wires, and the diameter of each barb 127 is relatively smaller, so that the perforation of the inner wall of the LAA is not easy to occur.

In the embodiment, the sealing disc 110 of the LAA occluder 100 has the waist part 112 and the disc surface 111 at the same time, and both of the waist part 112 and the disc surface 111 can achieve a function of occluding the opening of the LAA. Therefore, such double occlusion effect improves the integral occlusion function of the LAA occluder 100.

Figure 21A:
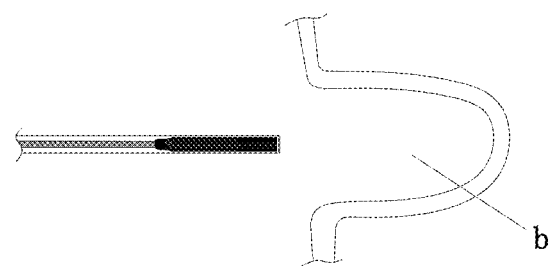
FIG. 21a is a schematic diagram of the anchoring net prepared to be released in embodiment 1.
Figure 21B:
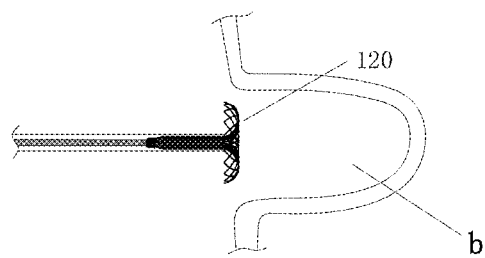
FIG. 21b is a schematic diagram of a constricted area of the anchoring net to be released in embodiment 1.
Figure 21C:
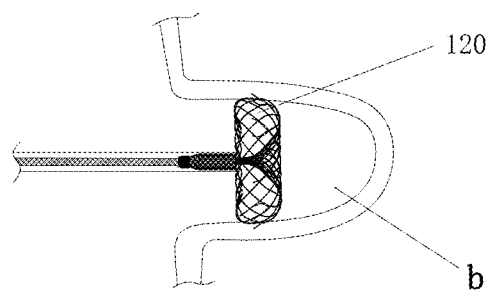
FIG. 21c is a schematic diagram of the anchoring net after the releasing is completed in embodiment 1.

In the embodiment, the LAA occluder 100 can be repeatedly released, and the releasing process is illustrated in FIG. 21a, FIG. 21b and FIG. 21c. In the transport device, the anchoring device is in a compression state. When the transport device moves to the opening of the LAA, the anchoring device is gradually released from the transport device. Due to the fact that the anchoring device is made from super elastic metal wires or shape memory alloy wires, after the constricted area on the outer layer of the anchoring net is separated from the transport device, the constricted area automatically rolls outwards, so that a contact part with the LAA wall always is a smooth surface. After the releasing of the anchoring device is completed, the barbs penetrate into the LAA wall, and the penetration directions of the barbs face the opening of the LAA.

Figure 22A:
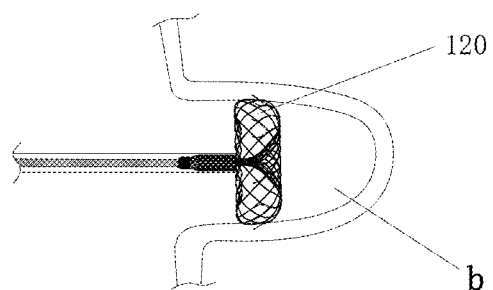
FIG. 22a is a schematic diagram of the anchoring device prepared to be withdrawn after the withdrawing of the sealing disc is completed in embodiment 1.
Figure 22B:
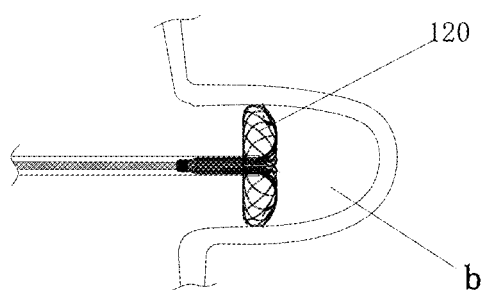
FIG. 22b is a schematic diagram of the anchoring device that is partially withdrawn in embodiment 1.
Figure 22C:
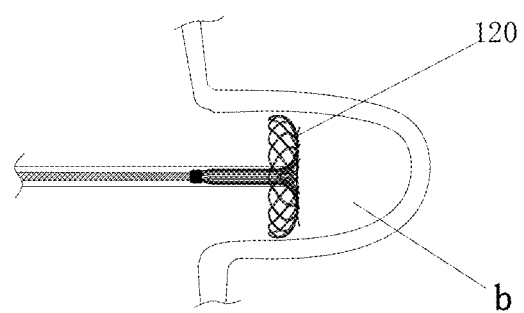
FIG. 22c is a schematic diagram of barbs that are completely withdrawn from the LAA wall in an anchoring device withdrawing process in embodiment 1.

If the releasing position of the LAA occluder is improper and the LAA occluder cannot achieve a great sealing effect, the LAA occluder needs to be withdrawn, and the withdrawing process is illustrated in FIG. 22a, FIG. 22b and FIG. 22c. In the LAA occluder withdrawing process, first the barbs are completely drawn out of the inner wall of the LAA opposite to the penetration directions, and then are accommodated in the transport device with the outer-layer anchoring net under the traction of the transport device.

As illustrated in FIG. 21a to FIG. 22c, b represents the LAA.

Embodiment 2

The difference between the embodiment 2 and the embodiment 1 is: each nickel-titanium wire 2221 for forming a barb and one reversed V-shaped nickel-titanium wire 2222 for forming a frame of an anchoring net are connected by welding. The length of a welded area 2223 is 2 mm, and the welded area 2223 is adjacent to an apex 2224, at which two sides of the reversed V-shaped nickel-titanium wire are intersected. An end part 2225, extending from the welded area 2223, of the nickel-titanium wire 2221 forms a barb 227, the length of the end part 2225 is 2 mm (namely H2=2 mm in FIG. 11b), and a distance between an end point 2226 of the end part 2225 and the apex 2224 of the reversed V-shaped nickel-titanium wire is 8 mm as illustrated in FIG. 11a, FIG. 11b, FIG. 12a and FIG. 12b.

Embodiment 3

The difference between the embodiment 3 and the embodiment 1 is: the total length of each nickel-titanium wire 3221 for forming a barb is 5 mm, and the nickel-titanium wire 3221 is divided into a fixed section and a free section. The fixed section is connected with the nickel-titanium wire 3222 for forming a frame of an anchoring device through a steel bushing 3223, the length of the fixed section is 3 mm, and the fixed section is completely inside the steel bushing 3223. The free section 3225 extends out of the steel bushing 3223 to form a barb 327, the length of the free section 3225 is 2 mm (namely H3=2 mm in FIG. 13b), and a distance between an end point 3226 of the free section 3225 and an apex 3224 of the reversed V-shaped nickel-titanium wire is 8 mm as illustrated in FIG. 13a, FIG. 13b, FIG. 14a and FIG. 14b.

Embodiment 4

Figure 15A:
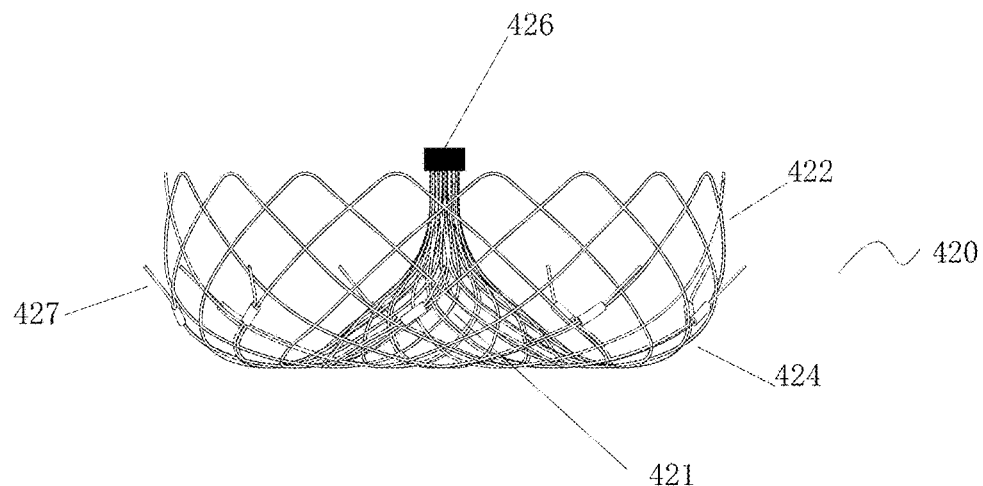
FIG. 15a is a schematic diagram of an anchoring device in embodiment 4.
Figure 15B:
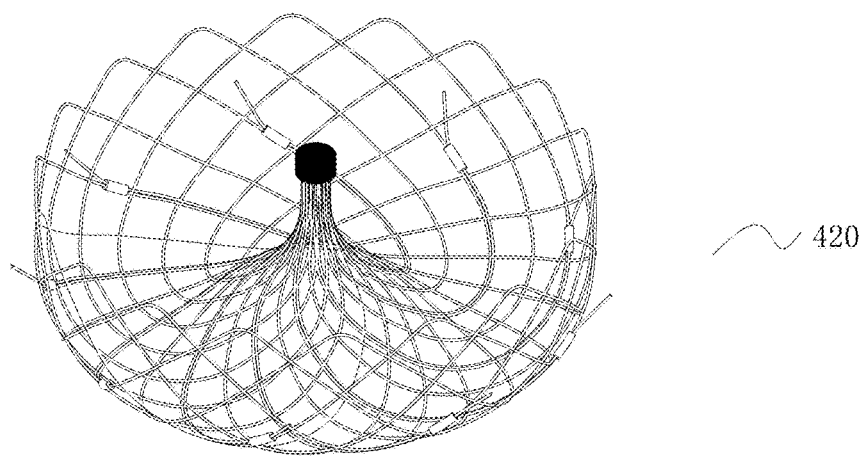
FIG. 15b is a schematic diagram of an anchoring device in embodiment 4 (from another perspective).

The difference between the embodiment 4 and the embodiment 1 is: an anchoring device 420 does not include a constricted area, and only includes a center end 426 connected with a sealing disc, a conical net 421 diffused from the center end 426 to a direction away from the sealing disc, and a nest-shaped anchoring net 422 located on the periphery of the conical net 421. The conical net 421 and the nest-shaped anchoring net 422 are smoothly connected through an arc transition area 424, and six barbs 427 are uniformly distributed on the surface of the nest-shaped anchoring net 422, as illustrated in FIG. 15a and FIG. 15b.

Embodiment 5

In this embodiment, an anchoring device 520 includes a center end 526 connected with a sealing disc, a conical net 521 diffused from the center end 526 to a direction away from the sealing disc, and a truncated-cone-shaped anchoring net 522 located on the periphery of the conical net 521. The conical net 521 and the truncated-cone-shaped anchoring net 522 are smoothly connected through an arc transition area 524, and six barbs 527 are uniformly distributed on the surface of the truncated-cone-shaped anchoring net 522.

The center end 526 is located at an axial end part of the conical net 521. One end, near the sealing disc, of the truncated-cone-shaped anchoring net 522 is connected with a constricted area 523 radially extending towards the center end 526, and the constricted area 523 and the truncated-cone-shaped anchoring net 522 are in smooth transition connection through an arc transition area 525.

Figure 16A:
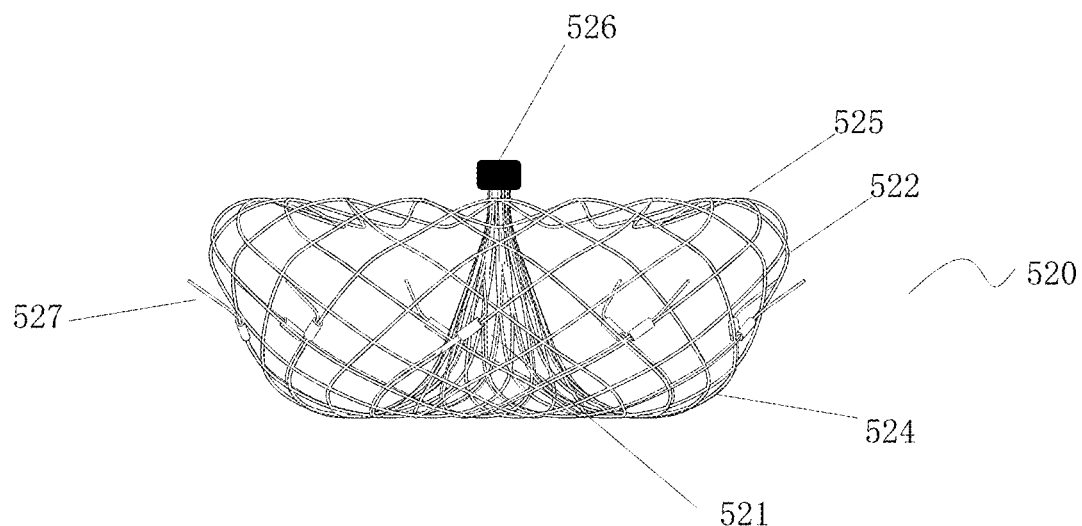
FIG. 16a is a schematic diagram of an anchoring device in embodiment 5.
Figure 16B:
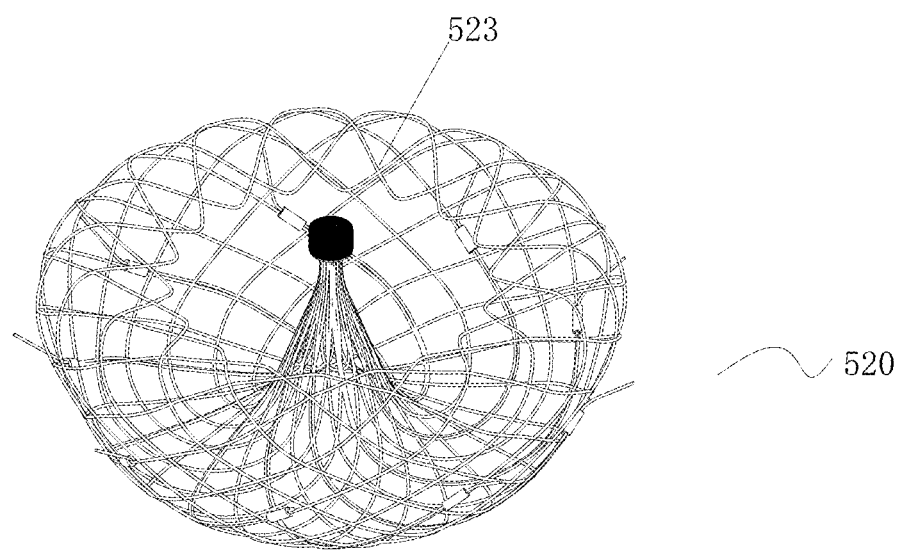
FIG. 16b is a schematic diagram of an anchoring device in embodiment 5 (from another perspective).

The difference between the embodiment 5 and the embodiment 1 is: the structure of the outer-layer anchoring net of the anchoring device 520 is truncated-cone-shaped 522, as illustrated in FIG. 16a and FIG. 16b.

Embodiment 6

In this embodiment, an anchoring device 620 includes a center end 626 connected with a sealing disc, a conical net 621 diffused from the center end 626 to a direction away from the sealing disc, and a curved ring-shaped anchoring net 622 located on the periphery of the conical net 621. The conical net 621 and the curved ring-shaped anchoring net 622 are smoothly connected through an arc transition area 624, and six barbs 627 are uniformly distributed on the surface of the curved ring-shaped anchoring net 622.

The center end 626 is located at an axial end part of the conical net 621, one end, near the sealing disc, of the curved ring-shaped anchoring net 622 is connected with a constricted area 623 radically extending towards the center end 626, and the constricted area 623 and the curved ring-shaped anchoring net 622 are in smooth transition connection through an arc transition area 625.

Figure 17A:
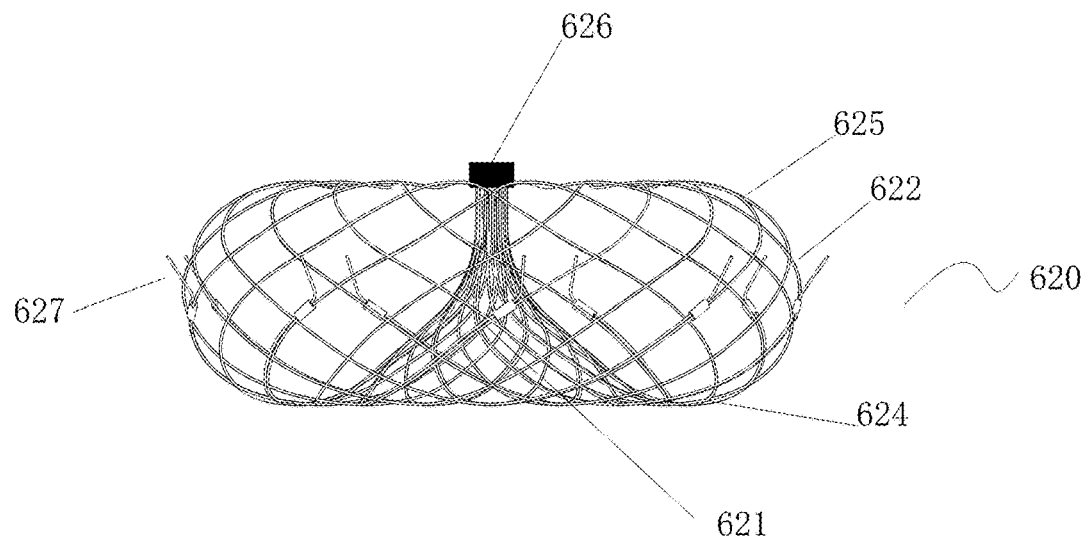
FIG. 17a is a schematic diagram of an anchoring device in embodiment 6.
Figure 17B:
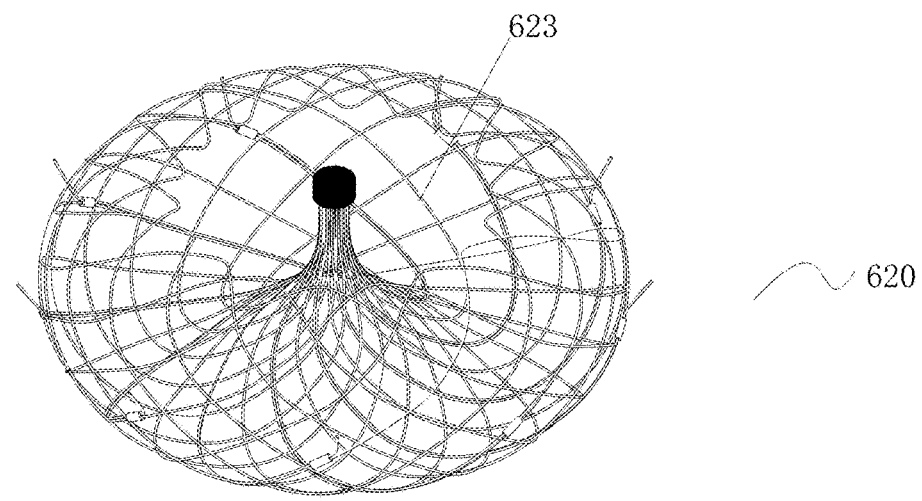
FIG. 17b is a schematic diagram of an anchoring device in embodiment 6 (from another perspective).

The difference between the embodiment 6 and the embodiment 1 is: the structure of the outer-layer anchoring net of the anchoring device 620 is curved ring-shaped 622, as illustrated in FIG. 17a and FIG. 17b.

Embodiment 7

Figure 18:
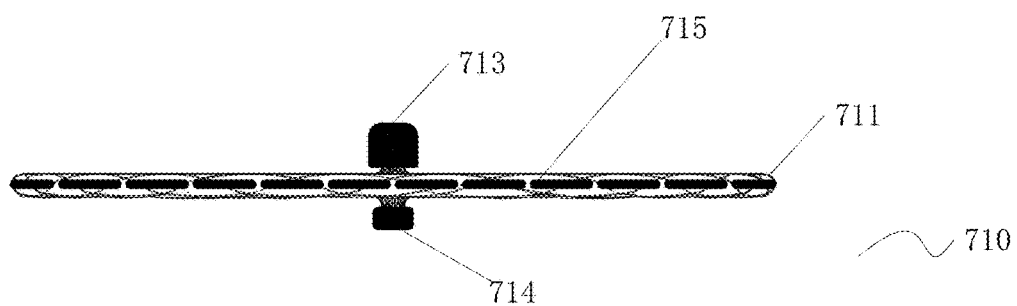
FIG. 18 is a schematic diagram of a sealing disc in embodiment 7.

The difference between the embodiment 7 and the embodiment 1 is: a sealing disc 710 only includes a disc surface 711. A first fixed end 713 and a second fixed end 714 are respectively arranged on the two sides of the disc surface 711, and one layer of PET flow blocking membrane 715 is sutured in the disc surface 711, as illustrated in FIG. 18.

Figure 19:
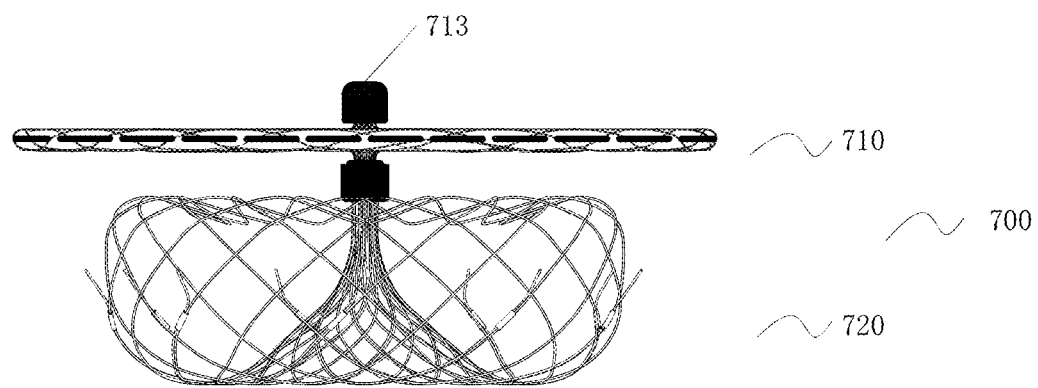
FIG. 19 is an integral schematic diagram of an LAA occluder in embodiment 7.

The second fixed end 714 of the disc surface 711 is connected with a center end of an anchoring net 720 through a steel bushing, as illustrated in FIG. 19.

Figure 20:
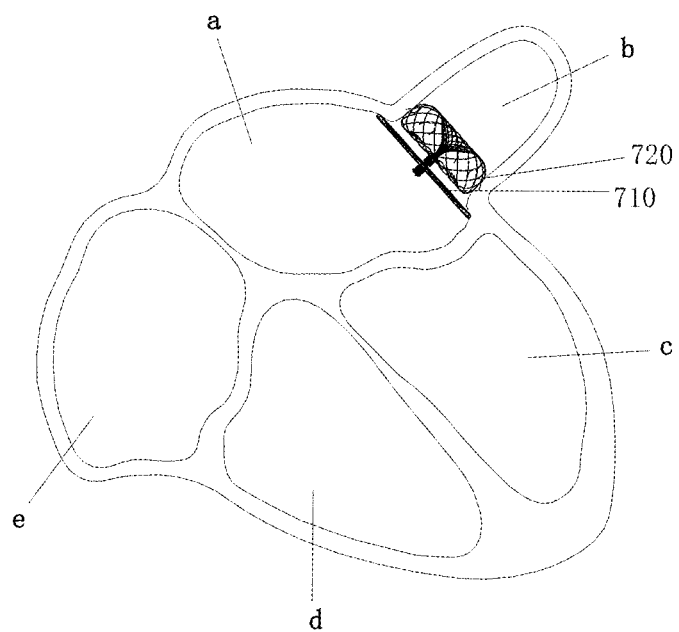
FIG. 20 is a schematic diagram of the LAA occluder released in the LAA in embodiment 7.

FIG. 20 is a schematic diagram of an LAA occluder 700 provided by this embodiment released in an LAA. In FIG. 20, a represents the left atrium, b represents the LAA, c represents the left ventricle, d represents the right ventricle, and e represents the right atrium.

What is claimed is:

1. A left atrial appendage (LAA) occluder, comprising a sealing disc and an anchoring device, both of which are mutually connected;
   wherein the sealing disc comprises a disc surface provided with a first fixed end for connecting a transport device and a waist part extending from the disc surface, wherein the waist part is provided with:
   a second fixed end;
   a diffusion section radiated and diffused outwards from the second fixed end; and
   a body section extending between an outer periphery of the disc surface and an outer periphery of the diffusion section, wherein the body section has a top edge extending radially outward to directly connect with the outer periphery of the disc surface, and a bottom edge connected with the outer periphery of the diffusion section; wherein the disc surface, the body section, and the diffusion section cooperate to define a cylindrical cavity within the waist part;
   wherein at least two layers of flow blocking membrane are arranged in the sealing disc, wherein one of the at least two layers of flow blocking membrane is sutured in the disc surface, and the other one of the at least two layer flow blocking membrane is sutured in the waist part and received in the cavity;
   wherein the anchoring device comprises a first end portion, a second end portion, and a body between the first end portion and the second end portion, wherein the first end portion is gathered together and welded to form a center end, the body extends outwards from the first end portion to form a conical net, and then gradually reverses outwards and extends towards the first end portion to form an anchoring net surrounding the conical net, wherein the anchoring net defines a first opening at the second end portion, and the center end extends out of the first opening to connect with the second fixed end of the sealing disc;
   wherein the anchoring device is capable of being released in an LAA, and the anchoring net is capable of cooperating with an inner wall of the LAA, and the anchoring net is of a backboneless structure;
   wherein the disc surface is capable of being positioned at an opening of the LAA and completely occluding, through the flow blocking membrane sutured in the disc surface, the opening of the LAA to prevent blood from flowing into the LAA; and
   wherein the waist part is capable of being received in a passage portion of the LAA communicating with the opening, to contact an inner wall of the passage portion, wherein the waist part is capable of occluding, through the flow blocking membrane sutured within the cavity of the waist part, the passage portion of the LAA to further prevent blood from flowing into the LAA.

2. The LAA occluder according to claim 1, wherein the anchoring device has a structure rolled from interior to exterior, an inner part of the rolled structure is formed as the conical net that is connected with the second fixed end portion of the sealing disc via the center end, and a periphery part of the rolled structure is formed as the anchoring net that is configured to cooperate with the LAA.

3. The LAA occluder according to claim 2, wherein the inner part is of a compressible hollow structure.

4. The LAA occluder according to claim 2, wherein the inner part is of a net-shaped structure or a multi-link structure.

5. The LAA occluder according to claim 2, wherein the anchoring net surrounds at least a half of the axial length of the inner part.

6. The LAA occluder according to claim 5, wherein the anchoring net surrounds to a part, near the first end portion, of the inner part in a rolling manner.

7. The LAA occluder according to claim 2, wherein the whole anchoring device is of a net-shaped structure.

8. The LAA occluder according to claim 7, wherein the anchoring device is formed by weaving a plurality of metal wires, and the metal wires are super elastic metal wires or shape memory alloy wires.

9. The LAA occluder according to claim 1, wherein the body extends outwards from the first end portion to form the conical net, then gradually reverses outwards to form an arc transition area, and then extends towards the first end portion to form the anchoring net surrounding the conical net, wherein the arc transition area is connected between the conical net and the anchoring net.

10. The LAA occluder according to claim 1, wherein the anchoring net is bowl-shaped, truncated-cone-shaped, or curved ring-shaped.

11. The LAA occluder according to claim 1, wherein the anchoring net is bent, at the second end portion, inwards to form a constricted area, wherein the constricted area defines the first opening.

12. The LAA occluder according to claim 1, wherein the anchoring net is provided with multiple barbs, and when the anchoring net is in an axial tension compression state, the barbs are arranged on an inner side surface of the anchoring net.

13. The LAA occluder according to claim 12, wherein the anchoring device is formed by weaving a plurality of first metal wires, the barbs and the first metal wires of the anchoring net are fixed by ferrule or fixed in a welding manner.

14. The LAA occluder according to claim 13, wherein the anchoring device further comprises a plurality of second metal wires attached to the first metal wires, wherein one end of each of the second metal wires extends to the first end portion of the anchoring device along an attached metal wire, and an opposite end of the second metal wire forms one of the barbs.

15. The LAA occluder according to claim 1, wherein the whole anchoring device is of a backboneless structure.

16. The LAA occluder according to claim 1, wherein the anchoring device is formed by cutting off metal tubes.

17. The LAA occluder according to claim 1, wherein the disc surface defines an inner space in which the one of the at least two layers of flow blocking membrane is sutured, wherein the flow blocking membrane sutured in the disc surface is perpendicular to an axis of the LAA occluder extending from the first fixed end to the second fixed end; and wherein the flow blocking membrane sutured within the cavity of the waist part is perpendicular to the axis of the LAA occluder;

wherein the second fixed end is arranged at a surface of the waist part away from the disc surface.

18. The LAA occluder according to claim 17, wherein the outer periphery of the diffusion section and the bottom edge of the body section are in arc transition.

19. The LAA occlude according to claim 18, wherein the at least two layers of flow blocking membrane comprise three layers of flow blocking membrane, one layer of flow blocking membrane is sutured in the disc surface, one layer of flow blocking membrane is sutured in the waist part and received in the cavity, and one layer of flow blocking membrane is located on the diffusion section.

* * * * *